(12) United States Patent
Palsson

(10) Patent No.: US 6,524,797 B1
(45) Date of Patent: Feb. 25, 2003

(54) METHODS OF IDENTIFYING THERAPEUTIC COMPOUNDS IN A GENETICALLY DEFINED SETTING

(76) Inventor: Bernhard O. Palsson, 730 Fern Glen, La Jolla, CA (US) 92037

( * ) Notice: Subject to any disclaimer, the term of this patent is extended or adjusted under 35 U.S.C. 154(b) by 0 days.

(21) Appl. No.: 09/568,595

(22) Filed: May 10, 2000

Related U.S. Application Data

(60) Provisional application No. 60/304,193, filed on May 10, 1999.

(51) Int. Cl.$^7$ .................. C12Q 1/68; G01N 33/53; C07H 21/04
(52) U.S. Cl. .................. 435/6; 435/7.1; 536/24.31; 536/24.33
(58) Field of Search ............ 435/6, 7.1; 536/24.31, 536/24.33

(56) References Cited

U.S. PATENT DOCUMENTS

| | | | |
|---|---|---|---|
| 5,134,062 A | | 7/1992 | Blass et al. ............. 435/7.21 |
| 5,561,047 A | * | 10/1996 | Shattil |
| 5,885,776 A | * | 3/1999 | Stone et al. ............. 435/6 |
| 6,087,107 A | * | 7/2000 | Sheffield et al. ............. 435/6 |
| 6,315,995 B1 | * | 11/2001 | Pinsky et al. ............. 424/94.63 |

FOREIGN PATENT DOCUMENTS

| | | |
|---|---|---|
| WO | WO 9000619 | 1/1990 |
| WO | WO 9102085 | 2/1991 |
| WO | WO 9115595 | 10/1991 |
| WO | WO 9305172 | 3/1993 |
| WO | WO 94/03602 | 2/1994 |
| WO | WO 94/29344 | 12/1994 |
| WO | WO 9719189 | 5/1997 |
| WO | WO 9720064 | 6/1997 |
| WO | WO 9727212 | 7/1997 |

OTHER PUBLICATIONS

Bogardus et al., "Pima Indians as a model to study the genetics of NIDDM" *J. Cell Biochem.* 48:337–343 (1992).

Desnottes, J.F., "New targets and strategies for the development of antibacterial agents" *TIBTECH* 14:134–140 (1996).

Francis, G.E., "Theoretical and practical considerations in screening strategies for differentiation agents" *Differentiation* 57:63–75 (1994).

Giuliano and Taylor, "Fluorescent–protein biosensors: new tools for drug discovery" *TIBTECH* 16:135–140 (1998).

Gonzalez and Negulescu, "Intracellular detection assays for high–throughput screening" *Curr. Opin. in Biotech* 9:624–631 (1998).

Hertzberg, R.P., "Whole cell assays in screening for biologically active substances" *Current Opinion in Biotechnology* 4:80–84 (1993).

Jayawickreme and Kost, "Gene expression systems in the development of high–throughput screens" *Curr. Opin. Biotech.* 8:629–634 (1997).

Major, J., "Challenges of High Throughput Screening Against Cell Surface Receptors" *J. Receptor & Signal Transduction Res.* 15(1–4):595–607 (1995).

Marshal, E., "Whose DNA Is It, Anyway?" *Science* 278:564–567 (1997).

Perlin et al., "The Plasma Membrane $H^+$–ATPase of Fungi" *Annals New York Academy of Sciences* 834:609–617 (1997).

Persidis, A., "High throughput screening" *Nature Biotechnology* 16:488–489 (1998).

Rice et al., "Development of a High Volume Screen to Identify Inhibitors of Endothelial Cell Activation" *Analytical Biochemistry* 241:254–259 (1996).

Rodrigues, A.D., "Preclinical Drug Metabolism in the Age of High–Throughput Screening: An Industrial Perspective" *Pharmaceutical Research* 14(11):1504–1510 (1997).

Sheffield et al., "Use of isolated inbred human populations for identification of disease genes" *Trends in Genetics* 14(10):391–396 (1998).

Smith, D.R., "Microbial pathogen genomes—new strategies for identifying therapeutics and vaccine targets" *TIBTECH* 14:290–293 (1996).

Sterrer and Henco, "Fluorescence Correlation Spectroscopy (FCS)—A Highly Sensitive Method to Analyze Drug–Target Interactions" *J. Receptor and Signal Transduction Res.* 17(1–3):511–520 (1997).

Taylor et al., "Linkage Analysis of Genetic Disorders" *Methods Mol. Biol.* 68:11–25 (1997).

Vuorio et al, "Familial hypercholesterolemia in the Finnish north Karelia. A molecular, clinical, and genealogical study" *Arterioscler. Thromb. Vasc. Biol.* 17:3127–3138 (1997).

Weeks and Lathrop, "Polygenic disease: methods for mapping complex disease traits" *Trends in Genetics* 11(12):513–519 (1995).

(List continued on next page.)

*Primary Examiner*—W. Gary Jones
*Assistant Examiner*—Arun KR. Chakrabarti
(74) *Attorney, Agent, or Firm*—Campbell & Flores LLP

(57) ABSTRACT

The invention provides a method of identifying therapeutic compounds in a genetically defined setting. The method consists of contacting a cell indicative of a pathological condition from a diseased individual and a cell from a genetically related normal individual with a plurality of candidate therapeutic compounds under suitable assay conditions, and identifying a compound that preferentially alters a predetermined property of the cell from the diseased individual.

82 Claims, 3 Drawing Sheets

OTHER PUBLICATIONS

Zamel et al., "Asthma on Tristan de Cunha: looking for the genetic link. The University of Toronto Genetics of Asthma Research Group" *Am. J. Respir. Crit. Care Med.* 153:1902–1906 (1996).

(Visited Dec. 16, 1998) <http://www.aurorabio.com/tech_platform–assay_technologies.html>.

(Visited Dec. 16, 1998) <http://www.aurorabio.com/tech_platform–uhtss_development.html>.

(Visited Dec. 16, 1998) <http://www.mdyn.com/arrays/ArrayImages.html>.

Gulcher and Stefansson, "Population genomics: laying the groundwork for genetic disease modeling and targeting," *Clin. Chem. Lab. Med.* 36(8):523–527 (1998).

Sumida et al., "Selective reduction of T cells bearing invariant Vα24JαQ antigen receptor in patients with systemic sclerosis," *J. Exp. Med.* 182:1163–1168 (1995).

\* cited by examiner

METHODS OF IDENTIFYING THERAPEUTIC COMPOUNDS IN A GENETICALLY DEFINED SETTING

This application is based on, and claims the benefit of, U.S. Provisional Application No. 60/304,193 (yet to be assigned), filed May 10, 1999, which was converted from U.S. Ser. No. 09/309,468, and entitled METHODS OF IDENTIFYING THERAPEUTIC COMPOUNDS IN A GENETICALLY DEFINED SETTING and which is incorporated herein by reference.

BACKGROUND OF THE INVENTION

The present invention relates generally to the fields of medicine and pharmacology and, more specifically, to methods of identifying therapeutic compounds in a genetically defined setting.

In the past, the process of discovering novel therapeutic compounds was slow and laborious, and usually involved administering individually synthesized compounds to experimental animals in the hope of observing a therapeutic effect. Recently, significant advances have been made in medicinal chemistry, resulting in the development of combinatorial chemistry methods that allow the rapid production of enormous libraries of structurally distinct compounds. Additionally, due to recent progress in understanding the underlying molecular mechanisms of many diseases, it has become possible to develop in vitro assays to rapidly screen candidate therapeutic compounds. Automation of these assays using computer-controlled robotic systems in high throughput screening methods has made it possible for biotechnology companies to screen millions of compounds per year.

The identification of therapeutic compounds using automated screening methods requires the development of in vitro assays that accurately predict the therapeutic potential of a compound identified by the assay for treatment of the particular pathological condition. So far, current drug screening methods have fallen short of this goal. For example, a variety of cell-free assays have been developed that focus on interactions of candidate compounds with isolated target molecules. Such assays have been shown to be of limited value, since neither the binding properties nor the expected biological properties of the compounds have usually proven to be relevant in vivo.

In an attempt to overcome the limitations of cell-free assays, a variety of cell-based assays have recently been developed. Such assays detect particular cellular functions believed to be relevant to the underlying disease mechanism. To date, however, most cell-based assays for screening candidate therapeutic compounds have used established cell lines. Established cell lines, as evidenced by their ability to be propagated indefinitely in culture, are highly abnormal and are often neoplastically transformed. Therefore, screening assays using such abnormal cell lines are poorly predictive of the therapeutic efficacy of compounds for affecting cell function in an individual.

Additionally, current cell-based assays to identify therapeutic compounds generally use cell lines established from a single individual, or cell lines established from unrelated normal and diseased individuals. Screening assays using cells from unrelated individuals are likely to identify compounds that alter a cellular function related to the genetic differences between the individuals, rather than compounds that alter a cellular function relevant to the underlying disease mechanism.

Therefore, there exists a need for improved methods of screening candidate therapeutic compounds. Ideally, such methods would use relevant cells and assay conditions so as to be highly predictive of the therapeutic efficacy of the compounds. The present invention satisfies this need and provides related advantages as well.

SUMMARY OF INVENTION

The invention provides a method of identifying a therapeutic compound potentially effective against a predetermined pathological condition. The method consists of contacting a cell indicative of the pathological condition from a diseased individual with a plurality of candidate therapeutic compounds under suitable assay conditions, and also contacting a cell indicative of the pathological condition from a normal individual, who is genetically related to the diseased individual, with the plurality of compounds under the same assay conditions. A compound from the plurality of compounds that preferentially alters a predetermined property of the cell from the diseased individual is identified, and characterized as a therapeutic compound potentially effective against the pathological condition.

DETAILED DESCRIPTION OF THE INVENTION

Figure 1:
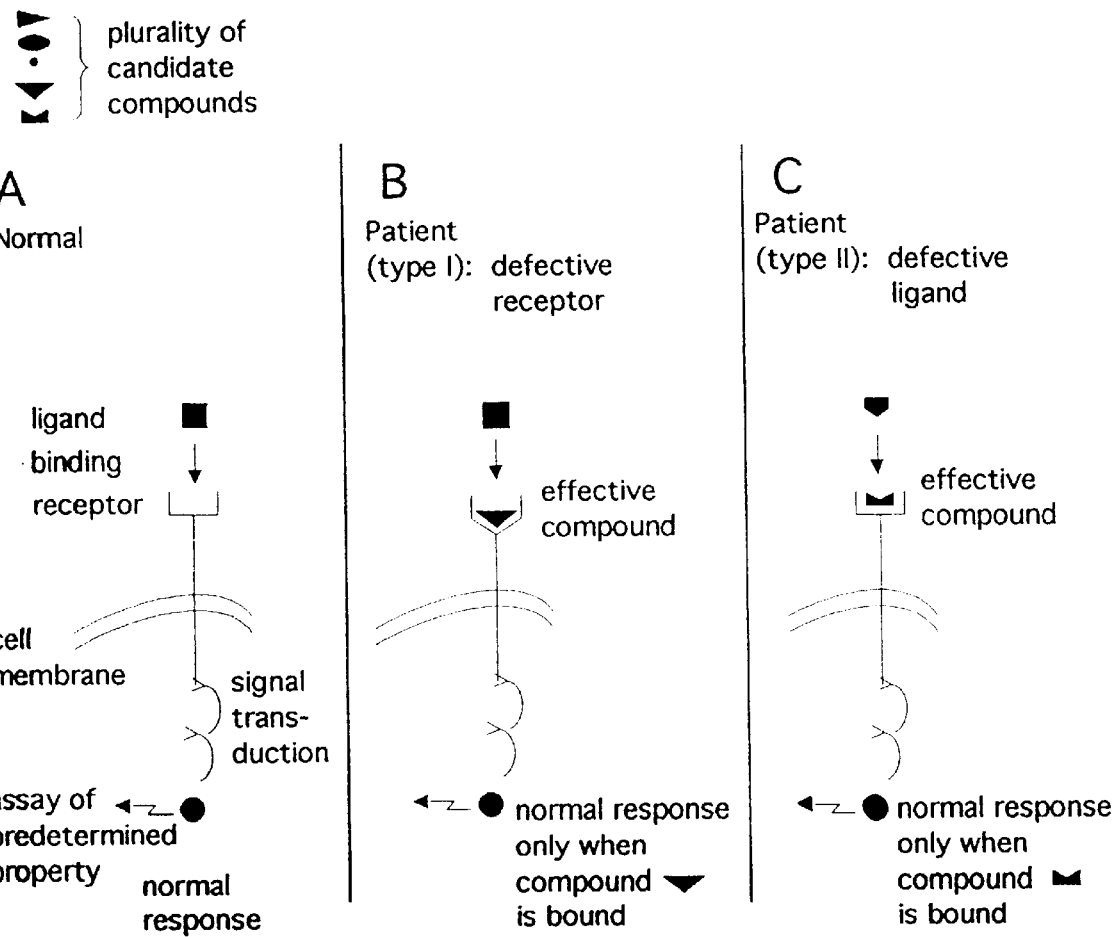
FIG. 1 shows a signal transduction pathway in a normal individual (Panel A) and two diseased individuals (Panels B and C).

The invention is directed to a method of identifying therapeutic compounds effective against a variety of pathological conditions. The method is advantageous in using primary cells obtained from genetically related normal and diseased individuals to screen candidate compounds. Therefore, variables due to genetic heterogeneity and abnormalities of established cell lines are minimized, and compounds identified by the method will have a high likelihood of being therapeutically effective in patients.

Specifically, the invention provides a method of identifying a therapeutic compound potentially effective against a predetermined pathological condition. The method consists of contacting a cell indicative of the pathological condition from a diseased individual with a plurality of candidate therapeutic compounds under suitable assay conditions, and also contacting a cell indicative of the pathological condition from a normal individual, who is genetically related to the diseased individual, with the plurality of compounds under the same assay conditions. A compound from the plurality of compounds that preferentially alters a predetermined property of the cell from the diseased individual is identified, and characterized as a therapeutic compound potentially effective against the pathological condition.

As used herein, the term "plurality of candidate therapeutic compounds" is intended to mean 2 or more different candidate therapeutic compounds. Such compounds can be used in a screening assay to identify one or more compounds that affect a predetermined property of a cell from a diseased individual to a greater extent than a cell from a normal individual. The number of different compounds in the plurality of compounds can be determined by those skilled in the art depending on the application of the method. For example, a smaller number of candidate compounds can be advantageous if the type of compound that is likely to affect a predetermined property of the cell is known or can be predicted. Additionally, if the method is used to compare the efficacy of compounds against cells from multiple normal or diseased individuals, it can be desirable to practice the method using a smaller number of compounds. Therefore, a plurality of compounds can include 2, 3, 4, 5, 10 or more, 20 or more, or 50 or more candidate compounds. Those skilled in the art also understand that the method can be practiced with a single compound, if desired.

However, when the type of compound that is likely to affect a predetermined property of the cell is unknown, it is generally understood that the larger the number of candidate therapeutic compounds, the greater the likelihood of identifying a therapeutic compound. Additionally, when the method is practiced using cells from only one or several diseased individuals, and one or several normal individuals, it may be desirable to screen a large number of different compounds. Therefore, a plurality of candidate therapeutic compounds can contain, for example, greater than about $10^3$ different compounds, preferably greater than about $10^5$ different compounds, more preferably, greater than about $10^7$ different compounds.

A candidate therapeutic compound can be a naturally occurring macromolecule, such as a polypeptide, nucleic acid, carbohydrate, lipid, or any combination thereof. A candidate therapeutic compound also can be a partially or completely synthetic derivative, analog or mimetic of such a macromolecule or, a small, synthetic molecule, such as an organic molecule prepared by combinatorial chemistry methods. A candidate compound can be detectably labeled or attached to a solid support, if desired, in a particular assay.

Methods for producing pluralities of compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse et al., U.S. Pat. No. 5,264,563; Francis et al., *Curr. Opin. Chem. Biol.* 2:422–428 (1998); Tietze et al., *Curr. Biol.*, 2:363–371 (1998); Sofia, *Mol. Divers.* 3:75–94 (1998); Eichler et al., *Med. Res. Rev.* 15:481–496 (1995); and the like. Libraries containing pluralities of candidate therapeutic compounds also can be obtained from commercial sources.

A therapeutic compound identified by a method of the invention is potentially effective in preventing or treating a predetermined pathological condition. As used herein, the term "pathological condition" is intended to mean a disease state characterized by aberrant physiological function or organization of cells, tissues or organs. A pathological condition can result, for example, from genetic or developmental abnormalities, nutritional or environmental factors, infection, neoplasia, aging, altered immune or endocrine function, tissue damage, or any combination of these factors. The invention is particularly amenable to identifying therapeutic compounds potentially effective against pathological conditions with a known hereditary component, and which affect a significant proportion of the population, such as, for example, asthma, cardiovascular disease, many types of cancer, schizophrenia, dementia, obesity, and diabetes. The invention can also be practiced with respect to rarer or monogenetic diseases such as, for example, diseases described in the Online Mendelian Inheritance in Man database (Center for Medical Genetics, Johns Hopkins University (Baltimore, Md.) and National Center for Biotechnology Information, National Library of Medicine (Bethesda, Md.) (1998)).

The methods of the invention are applicable to pathological conditions that affect all systems of the body, including, for example, the cardiovascular system, immune and hematopoietic system, respiratory system, hepatobiliary system, gastrointestinal system, endocrine system, urinary system, genital system, nervous system and musculoskeletal system. Certain pathologies are considered multisystem diseases and include, for example, systemic lupus erythematosus, systemic sclerosis, diabetes mellitus, and other inflammatory and metabolic disorders. Other diseases primarily or initially affect a single tissue or organ, such as a benign or malignant tumor of the breast, prostate, colon, lung, brain or ovary.

As used herein, the term "diseased individual" is intended to mean an individual exhibiting, or is considered to be at elevated risk, compared to the general population, of exhibiting signs or symptoms of a pathological condition. In contrast, as used herein, the term "normal individual" is intended to mean an individual who does not exhibit, or is considered to be at low risk of exhibiting, signs or symptoms of a pathological condition. The signs, symptoms and genetic and environmental risk factors associated with different pathological conditions are known in the art and are described, for example, in Stevens et al., ed., *Pathology*, Mosby:London (1995).

As used herein, the term "genetically related individual" is intended to mean an individual with a common ancestor within several generations. A more distantly genetically related individual can share an ancestor within 10 or fewer generations, such as 8 or fewer generations, preferably 6 or fewer generations. A more closely genetically related individual can share an ancestor within 4 or fewer generations, more preferably 3 or fewer generations, most preferably 2 or fewer generations. Genetically related individuals can be of the same generation, such as siblings, first cousins or distant cousins, or of different generations, such as a grandparents and grandchildren, parents and children, and aunt or uncle and niece or nephew.

The method is advantageous in that the effect of a compound on a cell from a diseased individual and a cell from a normal individual, genetically related to the diseased individual, is compared. Therefore, genetic variables unrelated to the pathological condition are minimized, which could otherwise complicate the interpretation of the screening assay. The more closely related a diseased and a normal individual are, the more likely it is that any difference observed is indicative of an effect on the pathological condition, rather than an effect of the compound on an irrelevant parameter. Therefore, when a method of the invention is practiced using a cell from a single diseased and a single normal individual, it is preferable to obtain samples from closely related individuals, such as siblings, more preferably fraternal twins, most preferably identical twins.

The invention can also advantageously be practiced using cells from multiple individuals selected from a large family or genetically homogeneous population that includes both normal and diseased individuals of varying degrees of relatedness. Using methods known in the art, the degree of relatedness of the individuals within the pedigree, and the relative risk for each individual within the pedigree of exhibiting the disease, can be established. The number of normal and diseased individuals and their degree of genetic relatedness can be determined by those skilled in the art for a particular application of the method. For example, the method can be practiced using cells from 2, 3, 4, 5, 10 or more, 20 or more, 50 or more, or 100 or more normal individuals, depending on the number of compounds being screened, the assay format, the ease of obtaining the samples, and the statistical significance required. Similarly, the method can be practiced using cells from 2, 3, 4, 5, 10 or more, 20 or more, 50 or more, or 100 or more diseased individuals.

In one embodiment, the invention can be practiced by obtaining cells from diseased individuals who each exhibit the same degree of severity of the pathological condition. In another embodiment, the diseased individuals can exhibit a range of severities of the pathological condition ranging, for example, from mildly affected to moderately affected to severely affected. For example, with regard to a disease such as cancer, cells could be obtained from diseased individuals who exhibit differing disease severities ranging from, for example, benign hyperplasia or dysplasia, to neoplasia, to a highly metastatic tumor.

In a further embodiment, the diseased individuals can exhibit a range of risk of developing the pathological condition ranging, for example, from a moderate risk of developing the pathological condition, to a high risk of developing the pathological condition, to actually exhibiting symptoms of the pathological condition. For example, in diseases with a hereditary component, the degree of risk can be related to the degree of relatedness to an affected individual. Furthermore, in diseases in which a susceptibility locus or gene has been identified, the degree of risk can be associated with the presence of none, one or two alleles of the susceptibility locus or gene. Similarly, in diseases with an environmental component, such as exposure to cigarette smoke, toxins, radioactivity, nutritional factors and the like, the degree of risk can be associated with the amount or extent of exposure to the environmental component.

Those skilled in the art can readily assess the degree of severity of the pathological condition for each individual and the degree of risk of developing the pathological condition for each individual, using knowledge of the risk factors, pathological mechanisms, and clinical signs and symptoms of a given disease. Those skilled in the art can also determine for a given application of the method the appropriate range of disease severity or risk, and the appropriate number of individuals with each degree of disease severity or risk. Factors involved in determining the number of individuals include, for example, the statistical significance of the data required, the qualitative or quantitative nature of the data obtained, and the availability of cells from a range of individuals for a given disease.

A method of the invention can advantageously be practiced using cells from individuals from genetically homogeneous populations, such as geographically isolated populations with relatively few founder individuals, or populations that are isolated for cultural or religious reasons. Isolated populations have had relatively little inward migration or intermarriage, and a result, most of the population is descended from the original founder individuals. Therefore, there is an increased likelihood that differences in the ability of therapeutic compounds to alter a property of cells of diseased and normal individuals will be related to the disease mechanism, rather than to cell-to-cell variations resulting from different genetic backgrounds. Additionally, environmental variation is likely to be minimal within isolated populations. Genetically homogeneous populations also advantageously include individuals with varying degrees of genetic relatedness, from distantly related to closely related. Therefore, the relative effect of a therapeutic compound on a property of a cell can be statistically analyzed and correlated with the degree of genetic relatedness.

Examples of genetically homogeneous populations of individuals are known in the art and include, for example, geographically isolated populations, such as island populations. Preferably, genetically homogeneous populations of individuals have extensive and accurate medical records and detailed genealogical records. Genetically homogeneous populations with extensive medical and genealogical records are well known in the art and include, for example, the population of Iceland, populations of the Scandinavian countries, the Mormon population of Utah, and the Amish and Hutterite populations of North America.

For certain diseases, epidemiological studies have been conducted among genetically homogeneous populations with an increased incidence of the disease. Therefore, a method of the invention can be practiced using cells obtained from diseased and normal individuals within such populations to identify therapeutically effective compounds against such diseases. As several non-limiting examples, it is known in the art that the population of Tristan de Cunha has an increased prevalence of asthma, as described in Zamel et al., *Am. J. Respir. Crit. Care Med.* 153:1902–1906 (1996); that the Pima Indians have an increased frequency of non-insulin dependent diabetes mellitus, as described in Bogardus et al., *J. Cell Biochem.* 48:337–343 (1992); that the population of Finnish North Karelia has an increased incidence of hypercholesteremia and coronary heart disease, as described in Vuorio et al., *Arterioscler. Thromb. Vasc. Biol.* 17:3127–3138 (1997); and that the population of the Central Valley of Costa Rica has increased prevalence of bipolar disorder, as described in Sheffield et al., *Trends in Genetics* 14:391–396 (1998). Other genetically homogeneous populations susceptible to particular pathological conditions of interest are known or can be determined by those skilled in the art.

The method is practiced by contacting a cell indicative of the predetermined pathological condition with the plurality of candidate therapeutic compounds under suitable assay conditions. As used herein, the term "cell indicative of a pathological condition" is intended to mean a cell that has, or can be made to have, one or more properties in a diseased individual that is detectably altered relative to a cell of the same histological origin from a normal individual. The term "a cell" is intended to include single cells, as well as pluralities of cells of the same or different histological type present in a cell suspension, cell culture, or tissue sample. The type and number of cells to use to identify a therapeutic compound will depend on the particular pathological condition and the assay used, and can be determined by those skilled in the art for a given application of the method.

A cell indicative of a pathological condition can be selected from a tissue or organ affected, or most affected, in the particular disease. Alternatively, a cell indicative of a pathological condition can be selected from an apparently unaffected tissue of a diseased individual. Many diseases, such as a genetic or multisystemic disorders, will be manifested in a variety of different tissues and cell types. Accordingly, it is not always necessary to know or to determine an affected, or the most affected, cell or tissue. Therefore, a cell indicative of many pathological conditions can be obtained from any convenient source. A factor to be determined in obtaining cells, particularly from a large number of normal and diseased individuals, is the ability to obtain the cells using minimally invasive methods. Therefore, cells from both normal and diseased individuals can readily be obtained, for example, from fluids such as the blood, lymph, urine or breast milk, or from accessible tissues such as the skin, hair follicles, cervix or cheek. Additionally, cells can readily be obtained from both normal and diseased individuals using slightly more invasive procedures, such as punch biopsies of the breast or muscle, or from the bone marrow or cerebrospinal fluid. Depending on the need and the availability of an appropriate surgical procedure, cells from essentially any organ or tissue of the body can be obtained from genetically related individuals and used in the methods of the invention.

Those skilled in the art can readily determine which cells are indicative of a pathological condition, which cells are appropriate control cells from normal individuals, and what is the most desirable source of such cells. Additionally, methods of obtaining, storing, culturing, and manipulating cells to ensure the introduction of the minimal amount of irrelevant variations between samples are well known in the art.

A cell indicative of a pathological condition can be a primary cell or tissue sample obtained directly from an individual. If desired, depending on the assay conditions employed, a cell indicative of a pathological condition can also be modified or altered from how it was initially obtained from the individual. For example, a cell indicative of a pathological condition can be a primary cell disaggregated from connective tissue and irrelevant cells using known methods, such as, for example enzymatic digestion and biochemical separation. Likewise, a cell indicative of a pathological condition can be a cell separated from other cells using affinity separation methods known in the art. As an example, flow cytometry or antibody panning methods can be used to select a population of cells expressing a detectable surface marker such as, for example, CD4, CD8, CD34 or CD38.

Additionally, a cell indicative of a pathological condition can be a cell propagated in culture, using methods known in the art, for several generations. Depending on the assay conditions employed, and as described below, such a cell can also be a cell that has been transduced or transfected with a nucleic acid encoding an expressible reporter construct, or contacted with a detectable molecule such as a radiolabeled compound or fluorochrome.

A cell from one or more diseased individuals and a cell from one or more normal individuals, selected as described above, are each contacted, either sequentially or simultaneously, with a candidate therapeutic compound under suitable assay conditions. As used herein, the term "suitable assay conditions" is intended to mean conditions under which a particular assay, such as an assay described below, will identify a compound that alters a predetermined property of a cell. Suitable assay conditions take into account factors such as the concentration of the compound, the duration of contact with the compound, the temperature and buffer conditions, the method of contact, whether or not cell viability is required, and the detection format. Suitable assay conditions depend on the cell type, the predetermined property to be detected, the pathological condition, and the number of compounds being screened. Assay conditions to identify compounds that alter predetermined properties of cells are known in the art or can be readily determined for a particular application of the method.

The method involves contacting a cell from a diseased individual and a cell from a genetically related normal individual under suitable assay conditions with a candidate compound, such that the effect of the compound on the predetermined property can be determined and a compound that preferentially alters the predetermined property of the cell from the diseased individual can be identified. The term "preferentially alter," as used herein, is intended to mean qualitatively or quantitatively changing the predetermined property of a cell from a diseased individual, relative to the same property of a cell from a normal individual.

As used herein, the term "predetermined property" is intended to mean a property that is known to be, or is considered by those skilled in the art to be, a credible indication of the particular pathological condition. The predetermined property to be detected can be chosen by those skilled in the art using knowledge of the underlying pathological mechanisms that are associated with the pathological condition. A predetermined property consistent with a method of the invention can be a biological process, a functional activity, or a structural property of the cell, so long as it is considered to be associated with the pathological condition and can be qualitatively or quantitatively detected in a cell-based in vitro assay.

For example, a predetermined property associated with a pathological condition can be a biological process such as cell proliferation, adhesion, differentiation, motility or apoptosis. Therefore, an appropriate assay would detect the ability of a compound to preferentially increase or inhibit such a process in cells from a diseased individual. Such biological assays generally involve initially viable cells, and assay conditions consistent with cell viability would be chosen.

An as example, a therapeutic agent potentially effective against cancer could be identified by screening candidate compounds against cells from an individual having, or a risk of developing, a neoplastic tumor, and against normal cells from related normal individuals. Compounds that preferentially exhibit cytotoxic or cytostatic activity against cells from the diseased individual, as determined by a reduction in cell number or viability, would be characterized as therapeutic compounds that are potentially effective against cancer.

A predetermined property associated with a pathological condition can also be a functional activity, such as, for example, altered production or turnover of a second messenger, GTP hydrolysis, influx or efflux of ions or amino acids, altered membrane voltage, increased or decreased protein phosphorylation, altered activity of an enzyme, altered protein-protein interactions, relocalization of a protein within the cell, or induction of gene expression, in response to contacting the cell with a therapeutically effective compound. Assays to detect alterations in these functional activities are well known in the art or can be readily adapted to a novel predetermined property relevant to a disease of interest. Such assays are described, for example, in Gonzalez et al., *Curr. Opin. in Biotech.* 9:624–631 (1998) and in Jayawickreme et al., *Curr. Opin. Biotech.* 8:629–634 (1997), and in references reviewed therein.

Often assays to detect a relevant functional activity involve first contacting the cell with a detectable biosensor, such as a fluorescent calcium indicator, green fluorescent protein, a fluorophore, a radiolabeled compound, or a chemiluminescent indicator, either alone or linked to another molecule such as an amino acid, peptide, oligosaccharide, nucleotide or nucleic acid. Additionally, such assays can involve first transducing the cells with a promoter-reporter nucleic acid construct such that, for example, β-lactamase, luciferase, green fluorescent protein or β-galactosidase will be expressed in response to contacting the cell with a therapeutically effective compound. Appropriate assays to detect functional activities preferentially altered in a diseased cell by a therapeutic compound can be determined by those skilled in the art based on knowledge of the underlying pathological mechanisms, such as knowledge of the signal transduction pathway or molecular interactions that underlie the pathology.

A predetermined property associated with a pathological condition can also be a structural property, such as the altered ability of a compound to bind a cell from a diseased individual. Therefore, a method of the invention can detect a compound that interacts with receptors present in increased or decreased abundance on the surface of cells from diseased individuals, or a compound that interacts with increased or decreased affinity with receptors present in equal abundance on the surface of cells from normal and diseased individuals. Such compounds can be either agonists or antagonists of the receptor.

Assays suitable for detecting various binding interactions are known in the art and include, for example, fluorescence correlation spectroscopy (FCS) and scintillation proximity assays (SPA), which are reviewed, for example, in Major, *J. Receptor and Signal Transduction Res.* 15:595–607 (1995); and in Sterrer et al., *J. Receptor and Signal Transduction Res.* 17:511–520 (1997). Other assays for detecting binding interactions include, for example, ELISA assays, FACS analysis, and affinity separation methods which are described, for example, in Harlow and Lane, Eds., *Antibodies: A Laboratory Manual*, Cold Spring Harbor Laboratory (1988). Such assays can often be performed with either viable or non-viable cells.

If desired, a method of the invention can be practiced using an assay wherein one or several steps, such as cell manipulation, culture plate manipulation, contacting the cells with the compounds, detection of the predetermined property, or statistical analysis of the data, are automated. Such automation advantageously provides for high throughput screening of candidate therapeutic compounds, often using smaller numbers of cells and smaller amounts of compounds and reagents than manual assays. Those skilled in the art can determine for a particular application of the method whether it would be advantageous to automate one or more steps of the screening assays. Methods of automating the assays described herein are well known in the art.

When the invention is practiced with a large number of compounds or with cells from a large number of individuals, or both, such as in a high-throughput screening format, the efficacy of compounds in altering a predetermined property in cells from normal and diseased individuals can be rank ordered and analyzed using known statistical methods. For example, when the invention is practiced with regard to a panel of cells from individuals with a range of disease severities, or with a range of disease risk, the effect of a compound in altering a predetermined property can be correlated with the disease severity or risk of the cells it affects, using, for example, statistical methods known within the art. Therefore, the method provides a means of rapidly identifying compounds that are potentially effective in preventing or treating a particular pathological condition in all individuals, most individuals, or only those individuals with a given degree of disease severity or risk. Additionally, the method can provide a means of comparing and ranking the potential of multiple compounds to be effective against a particular pathological condition in multiple individuals with varying degrees of disease severity or risk.

Statistical methods for analyzing the data obtained using the methods of the invention can be similar to methods used to map disease associated genes. Such statistical methods are described, for example, in Weeks et al., *Trends in Genetics* 11:513–519 (1995), in Taylor et al., *Methods Mol. Biol.* 68:11–25 (1997), and in Lynch and Walsh, *Genetics and Analysis of Quantitative Traits*, Sinauer Associates, Inc., Sunderland, Mass. (1998).

The method of identifying a therapeutic compound that preferentially alters the predetermined property of a cell from a diseased individual, from the plurality of candidate compounds, will depend on the number of compounds being tested and the particular assay employed. For example, the method of the invention can be repeated by subdividing pools of compounds into smaller pools, until a single compound that reproducibly preferentially alters a predetermined property of a cell from a diseased individual is identified. Alternatively, a compound that preferentially alters a predetermined property of the cell can be isolated away from the cell it affects and its identity determined. Additionally, a compound that preferentially alters a predetermined property of the cell can be identified by virtue of an inherent characteristic structural or functional property, or by virtue of a distinguishing label. These and other methods of identifying a potentially effective therapeutic compound resulting from practice of the method of the invention are known in the art.

A therapeutic compound identified by a method of the invention is potentially effective against the predetermined pathological condition. As used herein, the term "potentially effective" is intended to mean that a compound identified by a method of the invention has an increased likelihood, relative to a randomly chosen compound, to be effective in preventing or treating the pathological condition in vivo. Determining the actual efficacy of a potentially effective therapeutic compound is beyond the scope of the invention, as it is appreciated by the inventors that the safety and therapeutic efficacy of a compound must ultimately be determined by clinical trials in humans.

However, those skilled in the art can practice a method of the invention so as to increase the likelihood that a therapeutic compound will actually be effective in preventing or treating the disease in a clinical setting. For example, the efficacy of a therapeutic compound can be generalized by repeating the method using cells from additional genetically related normal and diseased individuals. Such individuals, if desired, can be from the same family or genetically homogeneous population initially used, or from different families or genetically related populations. Such individuals can exhibit, if desired, the same or varying degrees of disease severity or risk as the individuals whose cells were initially used in the method.

Additionally, the efficacy of the compound can be further validated by repeating the method using assays that detect alterations in one or more different predetermined properties associated with the pathological condition that the predetermined property initially assayed. Moreover, the method can be repeated using varying concentrations of a compound to determine the minimally effective and least toxic concentration. Therefore, the method can be used to identify those compounds that are most likely to be safe, effective and practical as therapeutics to prevent or treat a pathological condition.

It is understood that modifications which do not substantially affect the activity of the various embodiments of this invention are also included within the definition of the invention provided herein. Accordingly, the following examples are intended to illustrate but not limit the present invention.

EXAMPLE I

Identification of Therapeutic Compounds in a Genetically Defined Setting

Many human diseases have their origin in malfunctioning signal transduction pathways. A simple signal transduction pathway in a normal individual is shown in FIG. 1A, with an interaction between a ligand and a receptor initiating a cascade of intracellular signals that results in a normal response in an assay of a predetermined property. A defect in any one of these molecules, such as a ligand, a receptor, or an intracellular signaling molecule, can cause a pathological condition, which can be detected by an alteration in the predetermined property indicative of the pathological condition. The genetic relatedness between a normal individual and a diseased individual greatly enhances the probability that all the molecular components in the signaling cascade are similar or identical, except the component that causes the pathological condition.

As shown in FIG. 1B, a pathological condition can result from a defective receptor, indicated by the altered shape of the receptor as compared to the normal receptor in FIG. 1A. A compound that binds the abnormal receptor and allows it to interact with ligand, shown as a triangle, can restore normal signaling, as determined by a more normal response in an assay of a predetermined property. Other compounds in a plurality of candidate therapeutic compounds that do not restore interaction between the ligand and receptor will not affect the readout of the predetermined property in the diseased cell.

EXAMPLE II

Identification of Therapeutic Compounds Specific for Different Subtypes of a Pathological Condition A phenotypically similar pathological condition in individuals of genetically heterogeneous backgrounds can be caused by different underlying molecular mechanisms. For example, as shown in FIG. 1C, a phenotypically similar pathological condition to the pathological condition depicted in FIG. 1B can result from a defect in a different component of the signal transduction pathway, as indicated by the altered (non-square) shape of the ligand. A compound effective in a patient with the type I subtype of the pathology, indicated by a triangle in FIG. 1B, would not be able to restore normal signaling to a cell from a patient with the type II subtype of the pathology, and would not be an effective therapeutic compound for treating the type II subtype of the pathology. However, a compound that allows the defective ligand to interact with the receptor in a cell from a patient with the type II subtype of the pathology would restore normal signaling, and is a potentially effective therapeutic compound.

The methods of the invention can readily be applied to identifying potential therapeutic compounds that are effective against each of the different subtypes of the pathology, without prior knowledge of the molecular mechanisms that underly the different subtypes of the pathology. Thus, in the above example, cells from a genetically related population consisting of normal individuals and diseased individuals exhibiting the type I form of the pathology would be used in a screen to identify a therapeutic compound potentially effective against the type I form of the pathological condition. Likewise, cells from a genetically related population consisting of normal individuals and diseased individuals exhibiting the type II form of the pathology would be used in a screen to identify a therapeutic compound potentially effective against the type II form of the pathological condition.

The compounds so identified can be used as diagnostic reagents to determine the subtype of a pathology in a patient exhibiting clinical indications of the pathology. For example, the ability of a cell from a patient to give a normal response in an assay of a predetermined property in the presence of a compound that has been determined, as described above, to restore normal signaling in the type I subtype of the pathology, indicates that the patient has that subtype of the pathological condition. In contrast, the inability of a cell from a patient to give a normal response in an assay of a predetermined property in the presence of the same compound indicates that patient has a different subtype of the pathology. As described above, compounds that restore normal signaling in each of the different subtypes of the pathology can be determined, and these compounds can be used in diagnostic assays to identify the particular subtype of the pathology in each patient.

EXAMPLE III

Development of Combination Therapies

Figure 2:
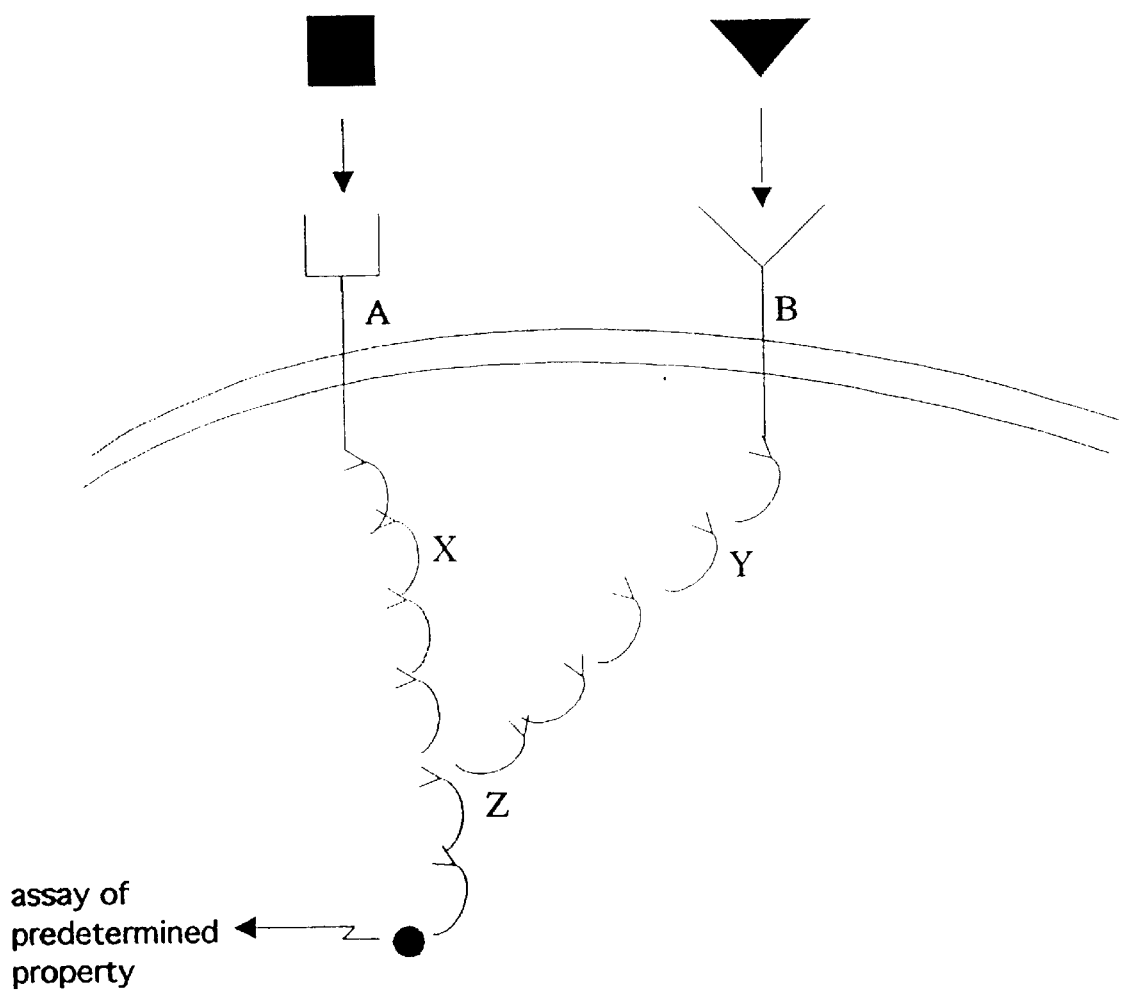
FIG. 2 shows two signal transduction pathways that together produce a signal in an assay of a predetermined property.

Most cellular functions involve multiple signal transduction pathways. Thus, the response in an assay of a predetermined property often requires the function of several convergent signaling pathways. Such a situation is shown in FIG. 2, where two ligands each bind their own receptor and initiate signaling cascades that converge to produce a signal in an assay of a predetermined property. In this example, the product of gene X, which carries out a process involved in one signaling transduction pathway, is a known disease associated gene. The products of genes Y and Z carry out processes involved in a second signal transduction pathway, and can be considered modifying factors of the effect of gene product X in an assay of a predetermined property.

In a genetically homogeneous population in which the diseased individuals have disease allele X, and normal individuals have wild-type allele X, the activities of gene products Y and Z are likely to be constant within the population, and the measurement of the predetermined property thus reflects the activity of X in each individual in that population. In contrast, in an outbred population, the measurement of the predetermined property reflects a varying contribution of the activities of X, Y and Z in each individual. Therefore, in a genetically homogeneous population, a therapeutic compound that targets gene product X can be identified. Additional screens in the presence of this compound can then be performed to identify compounds that affect the activities of modifying factors Y or Z, as measured by a further alteration in the readout in an assay of the predetermined property. Therefore, the invention provides a method of developing combination therapies that target both disease associated genes and their modifying factors.

In a different genetically homogeneous population, having different alleles or activities of modifying factors Y and Z, a similar screen performed in the presence of a compound that targets gene product X would likely identify different compounds that affect the activities of the modifying factors Y or Z in that population. Therefore, the invention provides a method of developing combination therapies that are specific for a patient's particular X, Y, and Z allele or activity combination.

EXAMPLE IV

Pathway Mapping of Disease-Associated Genes

In searching for a genetic basis for disease, methods have been developed to scan the genes of multiple individuals in a pedigree and to associate a marker on a locus with the disease history of the members of the pedigree. Such association are then used to map the disease-associated genes to a particular locus. The methods described herein can be used in a similar manner to map disease-associated genes to a "locus" of a signal transduction pathway.

Figure 3:
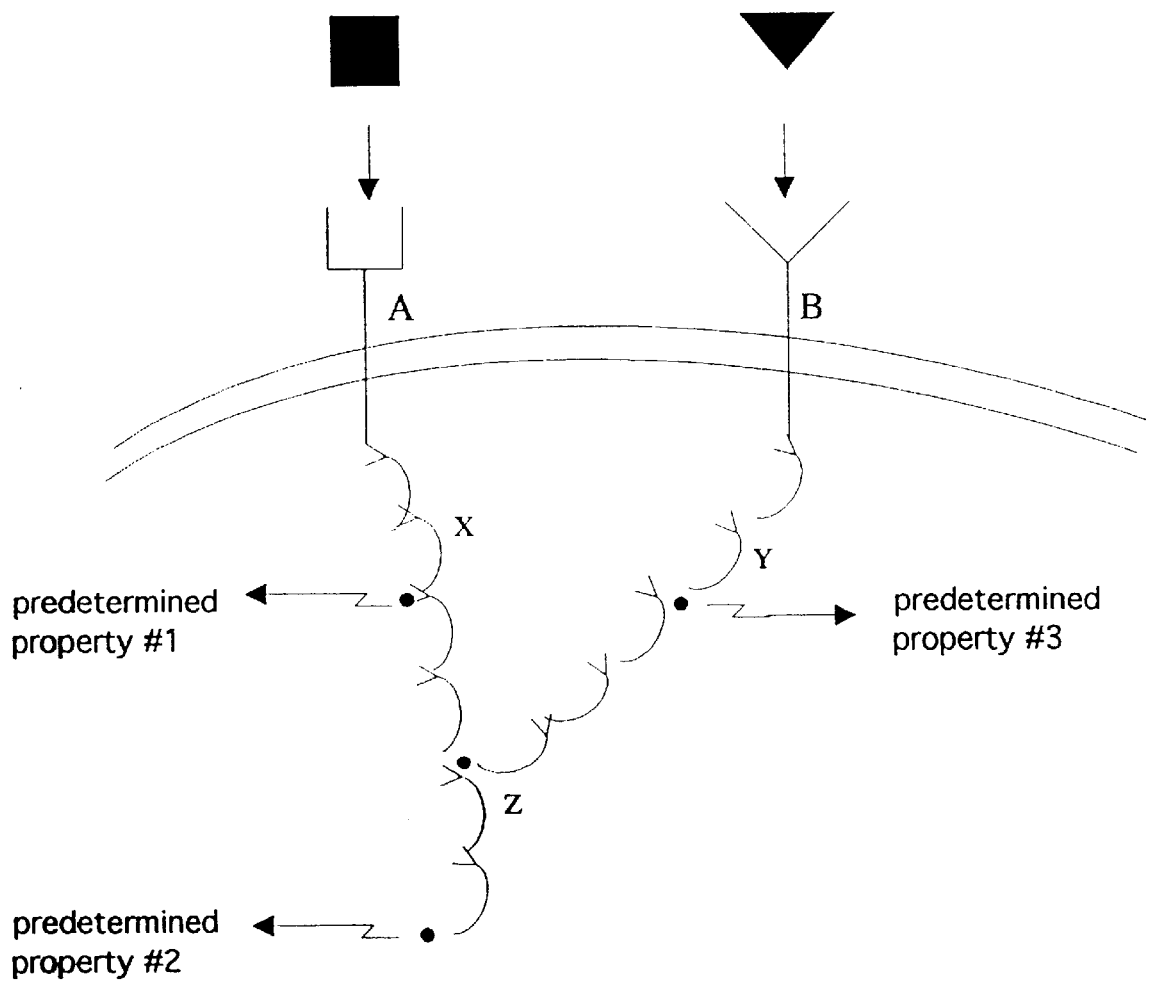
FIG. 3 shows a method of mapping disease associated gene products to loci of a signal transduction pathway.

As described herein, assays are known in the art that can be used to measure a predetermined property indicative of an alteration in any step of a signaling pathway, such as receptor/ligand interaction, second messenger signaling, phosphorylation events, gene expression and the like. For example, as shown in FIG. 3, three different predetermined properties representing three different loci within of a signaling pathway can be assayed. In a genetically homogeneous population, normal individuals and diseased individuals will have few differences in the molecules that carry out signaling steps, apart from the molecule responsible for the disease pathogenesis. Thus, by comparing several predetermined properties in normal and diseased cells from individuals in a genetically homogeneous population, the step in the signaling pathway that is altered in diseased individuals can be determined, and the disease-associated gene mapped to that "locus" of the signaling pathway. The disease-associated gene or gene product is likely to be an appropriate target in a high-throughput drug screening assay to identify compounds that can be used to treat the disease.

Throughout this application various publications have been referenced. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of identifying a therapeutic compound potentially effective against a predetermined pathological condition, comprising:
   (a) contacting, ex vivo, a cell indicative of said pathological condition from a diseased individual with a plurality of candidate therapeutic compounds under suitable assay conditions;
   (b) contacting, ex vivo, a control cell from a normal individual, genetically related to said diseased individual, with said plurality under said assay conditions; and
   (c) identifying a compound from said plurality that preferentially alters one or more predetermined properties of said cell from said diseased individual, said compound being characterized as a therapeutic compound potentially effective against said pathological condition.

2. The method of claim 1, wherein step (a) comprises contacting a cell from each of two or more genetically related diseased individuals.

3. The method of claim 2, wherein said two or more genetically related diseased individuals exhibit a range of disease severity or risk.

4. The method of claim 1, wherein step (b) comprises contacting a control cell from each of two or more genetically related normal individuals.

5. The method of claim 1, wherein step (a) comprises contacting a cell from each of two or more genetically related diseased individuals and step (b) comprises contacting a control cell from each of two or more genetically related normal individuals.

6. The method of claim 1, wherein said normal individual and said diseased individual are members of a genetically homogeneous population.

7. The method of claim 6, wherein said genetically homogeneous population is an Icelandic population.

8. The method of claim 1, wherein said plurality of candidate therapeutic compounds comprises greater than $10^5$ compounds.

9. The method of claim 1, wherein said pathological condition is selected from the group consisting of diseases of the cardiovascular system, nervous system, immune system, respiratory system, gastrointestinal system, endocrine system, and cancer.

10. The method of claim 1, wherein said method is automated.

11. The method of claim 1, wherein step (a) comprises contacting a cell from each of 10 or more genetically related diseased individuals.

12. The method of claim 1, wherein step (a) comprises contacting a cell from each of 100 or more genetically related diseased individuals.

13. The method of claim 1, wherein step (b) comprises contacting a control cell from each of 10 or more genetically related normal individuals.

14. The method of claim 1, wherein step (b) comprises contacting a control cell from each of 100 or more genetically related normal individuals.

15. The method of claim 1, wherein said normal individual and said genetically related diseased individual have a common ancestor within 6 or fewer generations.

16. The method of claim 1, wherein said normal individual and said genetically related diseased individual have a common ancestor within 2 or fewer generations.

17. The method of claim 1, wherein said normal individual and said genetically related diseased individual are of the same generation.

18. The method of claim 1, wherein said normal individual and said genetically related diseased individual are siblings.

19. The method of claim 1, wherein said normal individual and said genetically related diseased individual are of different generations.

20. The method of claim 1, wherein said normal individual and said genetically related diseased individual are related as parent and child.

21. The method of claim 1, wherein said plurality of candidate therapeutic compounds comprises greater than 50 compounds.

22. The method of claim 1, wherein said pathological condition is cancer.

23. The method of claim 1, wherein said predetermined property is selected from the group consisting of proliferation, adhesion, differentiation, motility and apoptosis.

24. The method of claim 1, wherein said cell is obtained from a tissue selected from the group consisting of breast, prostate, colon, lung, brain and ovary.

25. The method of claim 1, wherein said cell from said diseased individual is an unaffected cell.

26. The method of claim 1, wherein said cell from said diseased individual and said cell from said normal individual are propagated in culture.

27. The method of claim 1, wherein said cell from said diseased individual and said cell from said normal individual are transduced or transfected with a nucleic acid molecule.

28. The method of claim 1, further comprising:
(d) repeating steps (a) and (b) with said therapeutic compound obtained from step (c), and determining the ability of said therapeutic compound to preferentially alter a second or more predetermined property of said cell from said diseased individual.

29. A method of identifying a therapeutic compound potentially effective against a predetermined pathological condition, comprising:
(a) contacting, ex vivo, a cell indicative of said pathological condition from a diseased human individual with a plurality of candidate therapeutic compounds under suitable assay conditions;
(b) contacting, ex vivo, a control cell from a normal human individual, genetically related to said diseased human individual, with said plurality under said assay conditions; and
(c) identifying a compound from said plurality that preferentially alters one or more predetermined properties of said cell from said diseased human individual, said compound being characterized as a therapeutic compound potentially effective against said pathological condition.

30. The method of claim 29, wherein step (a) comprises contacting a cell from each of two or more genetically related diseased human individuals.

31. The method of claim 30, wherein said two or more genetically related diseased human individuals exhibit a range of disease severity or risk.

32. The method of claim 29, wherein step (b) comprises contacting a control cell from each of two or more genetically related normal human individuals.

33. The method of claim 29, wherein step (a) comprises contacting a cell from each of two or more genetically related diseased human individuals and step (b) comprises contacting a control cell from each of two or more genetically related normal human individuals.

34. The method of claim 29, wherein said normal human individual and said diseased human individual are members of a genetically homogeneous population.

35. The method of claim 34, wherein said genetically homogeneous population is an Icelandic population.

36. The method of claim 29, wherein said plurality of candidate therapeutic compounds comprises greater than $10^5$ compounds.

37. The method of claim 29, wherein said pathological condition is selected from the group consisting of diseases of the cardiovascular system, nervous system, immune system, respiratory system, gastrointestinal system, endocrine system, and cancer.

38. The method of claim 29, wherein said method is automated.

39. The method of claim 29, wherein step (a) comprises contacting a cell from each of 10 or more genetically related diseased human individuals.

40. The method of claim 29, wherein step (a) comprises contacting a cell from each of 100 or more genetically related diseased human individuals.

41. The method of claim 29, wherein step (b) comprises contacting a control cell from each of 10 or more genetically related normal human individuals.

42. The method of claim 29, wherein step (b) comprises contacting a control cell from each of 100 or more genetically related normal human individuals.

43. The method of claim 29, wherein said normal human individual and said genetically related diseased human individual have a common ancestor within 6 or fewer generations.

44. The method of claim 29, wherein said normal human individual and said genetically related diseased human individual have a common ancestor within 2 or fewer generations.

45. The method of claim 29, wherein said normal human individual and said genetically related diseased human individual are of the same generation.

46. The method of claim 29, wherein said normal human individual and said genetically related diseased human individual are siblings.

47. The method of claim 29, wherein said normal human individual and said genetically related diseased human individual are of different generations.

48. The method of claim 29, wherein said normal human individual and said genetically related diseased human individual are related as parent and child.

49. The method of claim 29, wherein said plurality of candidate therapeutic compounds comprises greater than 50 compounds.

50. The method of claim 29, wherein said pathological condition is cancer.

51. The method of claim 29, wherein said predetermined property is selected from the group consisting of proliferation, adhesion, differentiation, motility and apoptosis.

52. The method of claim 29, wherein said cell is obtained from a tissue selected from the group consisting of breast, prostate, colon, lung, brain and ovary.

53. The method of claim 29, wherein said cell from said diseased human individual is an unaffected cell.

54. The method of claim 29, wherein said cell from said diseased human individual and said cell from said normal human individual are propagated in culture.

55. The method of claim 29, wherein said cell from said diseased human individual and said cell from said normal human individual are transduced or transfected with a nucleic acid molecule.

56. The method of claim 29, further comprising:
(d) repeating steps (a) and (b) with said therapeutic compound obtained from step (c), and determining the ability of said therapeutic compound to preferentially alter a second or more predetermined property of said cell from said diseased human individual.

57. A method of identifying a therapeutic compound potentially effective against a predetermined pathological condition, comprising:
(a) contacting, ex vivo, a cell indicative of said pathological condition from a diseased human individual with a candidate therapeutic compound under suitable assay conditions;
(b) contacting, ex vivo, a control cell from a normal human individual, genetically related to said diseased human individual, with said candidate therapeutic compound under said assay conditions; and
(c) determining that said candidate therapeutic compound preferentially alters one or more predetermined properties of said cell from said diseased human individual, said candidate therapeutic compound being characterized as a therapeutic compound potentially effective against said pathological condition.

58. The method of claim 57, wherein step (a) comprises contacting a cell from each of two or more genetically related diseased human individuals.

59. The method of claim 58, wherein said two or more genetically related diseased human individuals exhibit a range of disease severity or risk.

60. The method of claim 57, wherein step (b) comprises contacting a control cell from each of two or more genetically related normal human individuals.

61. The method of claim 57, wherein step (a) comprises contacting a cell from each of two or more genetically related diseased human individuals and step (b) comprises contacting a control cell from each of two or more genetically related normal human individuals.

62. The method of claim 57, wherein said normal human individual and said diseased human individual are members of a genetically homogeneous population.

63. The method of claim 62, wherein said genetically homogeneous population is an Icelandic population.

64. The method of claim 57, wherein said pathological condition is selected from the group consisting of diseases of the cardiovascular system, nervous system, immune system, respiratory system, gastrointestinal system, endocrine system, and cancer.

65. The method of claim 57, wherein said method is automated.

66. The method of claim 57, wherein step (a) comprises contacting a cell from each of 10 or more genetically related diseased human individuals.

67. The method of claim 57, wherein step (a) comprises contacting a cell from each of 100 or more genetically related diseased human individuals.

68. The method of claim 57, wherein step (b) comprises contacting a control cell from each of 10 or more genetically related normal human individuals.

69. The method of claim 57, wherein step (b) comprises contacting a control cell from each of 100 or more genetically related normal human individuals.

70. The method of claim 57, wherein said normal human individual and said genetically related diseased human individual have a common ancestor within 6 or fewer generations.

71. The method of claim 57, wherein said normal human individual and said genetically related diseased human individual have a common ancestor within 2 or fewer generations.

72. The method of claim 57, wherein said normal human individual and said genetically related diseased human individual are of the same generation.

73. The method of claim 57, wherein said normal human individual and said genetically related diseased human individual are siblings.

74. The method of claim 57, wherein said normal human individual and said genetically related diseased human individual are of different generations.

75. The method of claim 57, wherein said normal human individual and said genetically related diseased human individual are related as parent and child.

76. The method of claim 57, wherein said pathological condition is cancer.

77. The method of claim 57, wherein said predetermined property is selected from the group consisting of proliferation, adhesion, differentiation, motility and apoptosis.

78. The method of claim 57, wherein said cell is obtained from a tissue selected from the group consisting of breast, prostate, colon, lung, brain and ovary.

79. The method of claim 57, wherein said cell from said diseased human individual is an unaffected cell.

80. The method of claim 57, wherein said cell from said diseased human individual and said cell from said normal human individual are propagated in culture.

81. The method of claim 57, wherein said cell from said diseased human individual and said cell from said normal human individual are transduced or transfected with a nucleic acid molecule.

82. The method of claim 57, further comprising:
(d) repeating steps (a) and (b) with said therapeutic compound obtained from step (c), and determining the ability of said therapeutic compound to preferentially alter a second or more predetermined property of said cell from said diseased human individual.

* * * * *